(12) United States Patent
Folger et al.

(10) Patent No.: US 8,920,820 B2
(45) Date of Patent: Dec. 30, 2014

(54) HIGHLY CONCENTRATED STABLE MELOXICAM SOLUTIONS FOR NEEDLELESS INJECTION

(71) Applicants: Martin A. Folger, Ingelheim am Rhein (DE); Stefan Henke, Kirchen (DE); Bernhard Hassel, Ockenheim (DE); Bernd Zierenberg, Bingen am Rhein (DE)

(72) Inventors: Martin A. Folger, Ingelheim am Rhein (DE); Stefan Henke, Kirchen (DE); Bernhard Hassel, Ockenheim (DE); Bernd Zierenberg, Bingen am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 0 days.

(21) Appl. No.: 14/078,953

(22) Filed: Nov. 13, 2013

(65) Prior Publication Data

US 2014/0113893 A1    Apr. 24, 2014

Related U.S. Application Data

(63) Continuation of application No. 11/845,675, filed on Aug. 27, 2007, now abandoned, which is a continuation of application No. 10/314,586, filed on Dec. 9, 2002, now abandoned.

(30) Foreign Application Priority Data

Dec. 12, 2001 (DE) .................................. 101 61 077

(51) Int. Cl.
| | | |
|---|---|---|
| A61K 9/00 | (2006.01) | |
| A61K 31/54 | (2006.01) | |
| A61K 47/10 | (2006.01) | |
| A61K 47/18 | (2006.01) | |
| A61K 31/5415 | (2006.01) | |

(52) U.S. Cl.
CPC ........... *A61K 31/5415* (2013.01); *A61K 9/0021* (2013.01); *A61K 47/10* (2013.01); *A61K 47/183* (2013.01)
USPC ........................................ 424/400; 514/226.5

(58) Field of Classification Search
USPC ........................................ 424/400; 514/226.5
See application file for complete search history.

(56) References Cited

U.S. PATENT DOCUMENTS

| | | | |
|---|---|---|---|
| 2,795,529 A | 6/1957 | Alburn et al. | |
| 3,288,675 A | 11/1966 | Newmark et al. | |
| 3,849,549 A | 11/1974 | Dempski et al. | |
| 3,931,212 A | 1/1976 | Satzinger et al. | |
| 3,947,576 A | 3/1976 | Kuczkowski et al. | |
| 4,233,299 A | 11/1980 | Trummlitz et al. | |
| 4,482,554 A | 11/1984 | Gebhardt et al. | |
| 4,628,053 A | 12/1986 | Fries | |
| 4,748,174 A | 5/1988 | Veronesi | |
| 4,794,117 A | 12/1988 | Corbiere | |
| 4,835,187 A | 5/1989 | Reuter et al. | |
| 4,942,167 A | 7/1990 | Chiesi et al. | |
| 5,169,847 A | 12/1992 | Nagy nee Kricsfalussy et al. | |
| 5,178,878 A | 1/1993 | Wehling et al. | |
| 5,283,065 A | 2/1994 | Doyon et al. | |
| 5,304,561 A | 4/1994 | Sarfarazi | |
| 5,360,611 A | 11/1994 | Robertson et al. | |
| 5,414,011 A | 5/1995 | Fu et al. | |
| 5,489,439 A | 2/1996 | Bola | |
| 5,654,003 A | 8/1997 | Fuisz et al. | |
| 5,700,816 A | 12/1997 | Isakson et al. | |
| 5,811,446 A | 9/1998 | Thomas | |
| 5,824,658 A | 10/1998 | Falk et al. | |
| 5,886,030 A | 3/1999 | Maniar | |
| 6,046,191 A | 4/2000 | Hamley et al. | |
| 6,071,539 A | 6/2000 | Robinson et al. | |
| 6,090,800 A | 7/2000 | Unger et al. | |
| 6,106,862 A | 8/2000 | Chen et al. | |
| 6,136,804 A | 10/2000 | Nichtberger | |
| 6,156,349 A | 12/2000 | Steinbach et al. | |
| 6,166,012 A | 12/2000 | Muller et al. | |
| 6,180,136 B1 | 1/2001 | Larson et al. | |
| 6,183,779 B1 | 2/2001 | Ouali et al. | |
| 6,184,220 B1 | 2/2001 | Turck et al. | |
| 6,187,800 B1 | 2/2001 | Suri et al. | |
| 6,221,377 B1 | 4/2001 | Meyer | |
| 6,284,269 B1 | 9/2001 | Struengmann et al. | |
| 6,495,603 B1 | 12/2002 | Miyake et al. | |
| 6,599,529 B1 | 7/2003 | Skinhøj et al. | |
| 6,605,295 B1 | 8/2003 | Bellmann et al. | |
| 6,630,056 B1 | 10/2003 | Thibierge et al. | |
| 6,669,957 B1 | 12/2003 | Laruelle et al. | |
| 6,682,747 B1 | 1/2004 | Turck et al. | |
| 6,869,948 B1 | 3/2005 | Bock et al. | |
| 6,986,346 B2 | 1/2006 | Hochrainer et al. | |

(Continued)

FOREIGN PATENT DOCUMENTS

| | | |
|---|---|---|
| AU | 673675 B2 | 11/1996 |
| CA | 1102802 | 6/1981 |

(Continued)

OTHER PUBLICATIONS

Winfield, Pharmaceutical Practice, Ophthalmic Products—Chelating agents, Churchill Livingstone, 2004, 268.*

(Continued)

*Primary Examiner* — Gigi Huang

(74) *Attorney, Agent, or Firm* — Michael P. Morris; Joyce L. Morrison

(57) ABSTRACT

An aqueous cyclodextrin-free solution of meloxicam suitable is provided for administration by needleless injection, containing a pharmacologically acceptable meloxicam salt of an organic or inorganic base and one or more suitable excipients.

9 Claims, No Drawings

(56) References Cited

U.S. PATENT DOCUMENTS

| | | |
|---|---|---|
| 7,105,512 B2 | 9/2006 | Morizono et al. |
| 7,969,206 B2 | 6/2011 | Ito |
| 2001/0055569 A1 | 12/2001 | Davis et al. |
| 2002/0006440 A1 | 1/2002 | Cherukuri |
| 2002/0016342 A1 | 2/2002 | Scolnick et al. |
| 2002/0035107 A1 | 3/2002 | Henke et al. |
| 2002/0058908 A1 | 5/2002 | Zierenberg et al. |
| 2002/0068088 A1 | 6/2002 | Gruber |
| 2002/0077328 A1 | 6/2002 | Hassan et al. |
| 2002/0099049 A1 | 7/2002 | Burch et al. |
| 2002/0106345 A1 | 8/2002 | Uhrich et al. |
| 2002/0187187 A1 | 12/2002 | Ohki et al. |
| 2003/0055051 A1* | 3/2003 | Morizono et al. ......... 514/226.5 |
| 2003/0109701 A1 | 6/2003 | Coppi et al. |
| 2003/0119825 A1 | 6/2003 | Folger et al. |
| 2003/0199482 A1 | 10/2003 | Seibert et al. |
| 2003/0220306 A1 | 11/2003 | Simmons et al. |
| 2004/0001883 A1 | 1/2004 | Matsui et al. |
| 2004/0015126 A1 | 1/2004 | Zierenberg et al. |
| 2004/0024041 A1 | 2/2004 | Selzer |
| 2004/0024042 A1 | 2/2004 | Breyer |
| 2004/0037869 A1 | 2/2004 | Cleverly et al. |
| 2004/0043992 A1 | 3/2004 | Tolba et al. |
| 2004/0110747 A1 | 6/2004 | Altman |
| 2004/0170687 A1 | 9/2004 | Hurd et al. |
| 2004/0171611 A1 | 9/2004 | Trummlitz et al. |
| 2004/0180092 A1 | 9/2004 | Henke et al. |
| 2004/0198826 A1 | 10/2004 | Baiker et al. |
| 2004/0204413 A1 | 10/2004 | Faour et al. |
| 2004/0204472 A1 | 10/2004 | Briggs et al. |
| 2004/0214753 A1 | 10/2004 | Britten et al. |
| 2004/0229038 A1 | 11/2004 | Cooper et al. |
| 2004/0234596 A1 | 11/2004 | Ohki et al. |
| 2004/0253312 A1 | 12/2004 | Sowden et al. |
| 2005/0038018 A1 | 2/2005 | Kanbe et al. |
| 2005/0187212 A1 | 8/2005 | Ohki et al. |
| 2005/0187213 A1 | 8/2005 | Lang et al. |
| 2005/0197332 A1 | 9/2005 | Altman |
| 2005/0244491 A1 | 11/2005 | Ohki et al. |
| 2005/0245510 A1 | 11/2005 | Friton et al. |
| 2005/0277634 A1 | 12/2005 | Janott et al. |
| 2005/0288280 A1 | 12/2005 | Friton et al. |
| 2006/0079516 A1 | 4/2006 | Henke et al. |
| 2006/0160793 A1 | 7/2006 | Altman |
| 2006/0217431 A1 | 9/2006 | Daemmgen et al. |
| 2007/0077296 A1 | 4/2007 | Folger et al. |
| 2007/0099907 A1 | 5/2007 | Altman |
| 2008/0132493 A1 | 6/2008 | Folger et al. |
| 2008/0234380 A1 | 9/2008 | Shapiro |
| 2008/0280840 A1 | 11/2008 | Lang et al. |
| 2011/0083985 A1 | 4/2011 | Folger et al. |
| 2011/0275618 A1 | 11/2011 | Folger et al. |
| 2012/0077764 A1 | 3/2012 | Freehauf et al. |
| 2013/0178467 A1 | 7/2013 | Henke et al. |
| 2014/0066440 A1 | 3/2014 | Folger et al. |
| 2014/0113893 A1 | 4/2014 | Folger et al. |

FOREIGN PATENT DOCUMENTS

| | | |
|---|---|---|
| CA | 2164100 A1 | 1/1995 |
| CA | 2166204 A1 | 1/1995 |
| CA | 2326517 A1 | 10/1999 |
| CA | 2404360 A1 | 9/2001 |
| CA | 2414063 A1 | 12/2001 |
| CA | 2469588 | 6/2003 |
| CA | 2503396 A1 | 5/2004 |
| DE | 3434707 A1 | 4/1985 |
| DE | 3700172 A1 | 7/1987 |
| DE | 4217971 C1 | 10/1993 |
| DE | 19729879 A1 | 1/1999 |
| DE | 10010123 A1 | 9/2001 |
| DE | 10024752 A1 | 11/2001 |
| DE | 10032132 A1 | 1/2002 |
| DE | 10300323 A1 | 10/2004 |
| EP | 0002482 A1 | 6/1979 |
| EP | 0034432 A2 | 8/1981 |
| EP | 0093999 A2 | 11/1983 |
| EP | 0177870 A2 | 4/1986 |
| EP | 0179430 A2 | 4/1986 |
| EP | 0306984 A1 | 3/1989 |
| EP | 0360246 A1 | 3/1990 |
| EP | 0390071 A1 | 10/1990 |
| EP | 0422681 A1 | 4/1991 |
| EP | 0465235 A1 | 1/1992 |
| EP | 0560329 A1 | 9/1993 |
| EP | 0945134 A1 | 9/1999 |
| EP | 1082966 A1 | 3/2001 |
| EP | 1190714 A2 | 3/2002 |
| EP | 1568369 A1 | 8/2005 |
| ES | 2065846 A1 | 2/1995 |
| ES | 2159564 T3 | 10/2001 |
| FR | 2437838 A1 | 4/1980 |
| GB | 2455875 A | 6/2009 |
| IT | 1251650 B | 5/1995 |
| JP | 47007352 Y1 | 3/1972 |
| JP | 1299230 A | 12/1989 |
| JP | 11139971 A | 5/1999 |
| JP | 2001170083 A | 6/2001 |
| JP | 2001172183 A | 6/2001 |
| JP | 2003535902 A | 12/2003 |
| JP | 3550782 B2 | 8/2004 |
| JP | 4018022 B2 | 12/2007 |
| JP | 04321624 B2 | 8/2009 |
| WO | 9301814 A1 | 2/1993 |
| WO | 9400420 A1 | 1/1994 |
| WO | 9509639 A1 | 4/1995 |
| WO | 9517178 A1 | 6/1995 |
| WO | 9518604 A1 | 7/1995 |
| WO | 9603387 A1 | 2/1996 |
| WO | 9603388 A1 | 2/1996 |
| WO | 9610999 A2 | 4/1996 |
| WO | 9611192 A1 | 4/1996 |
| WO | 9641625 A1 | 12/1996 |
| WO | 9703655 A1 | 2/1997 |
| WO | 9703667 A1 | 2/1997 |
| WO | 9717978 A1 | 5/1997 |
| WO | 9717989 A1 | 5/1997 |
| WO | 9729776 A1 | 8/1997 |
| WO | 9731631 A1 | 9/1997 |
| WO | 9817250 A1 | 4/1998 |
| WO | 9909988 A1 | 3/1999 |
| WO | 9912524 A1 | 3/1999 |
| WO | 9927906 A1 | 6/1999 |
| WO | 9949845 A1 | 10/1999 |
| WO | 9949867 A1 | 10/1999 |
| WO | 9959634 A1 | 11/1999 |
| WO | 0015195 A1 | 3/2000 |
| WO | 0108689 A1 | 2/2001 |
| WO | 0137838 A1 | 5/2001 |
| WO | WO 0137838 A1 * | 5/2001 |
| WO | 0152897 A2 | 7/2001 |
| WO | 0164268 A1 | 9/2001 |
| WO | 0187343 A2 | 11/2001 |
| WO | 0197813 A2 | 12/2001 |
| WO | 02085331 A1 | 10/2002 |
| WO | 03049733 A1 | 6/2003 |
| WO | 03082297 A1 | 10/2003 |
| WO | 03097066 A1 | 11/2003 |
| WO | 2004004776 A1 | 1/2004 |
| WO | 2004026116 A2 | 4/2004 |
| WO | 2004026313 A1 | 4/2004 |
| WO | 2004037264 A1 | 5/2004 |
| WO | 2004089379 A2 | 10/2004 |
| WO | 2004103283 A2 | 12/2004 |
| WO | 2005002542 A2 | 1/2005 |
| WO | 2005004915 A2 | 1/2005 |
| WO | 2005079806 A1 | 9/2005 |
| WO | 2005105101 | 11/2005 |
| WO | 2005115386 A1 | 12/2005 |
| WO | 2006000306 A1 | 1/2006 |
| WO | 2006100213 A1 | 9/2006 |
| WO | 2007039417 A1 | 4/2007 |
| WO | 2007087214 A1 | 8/2007 |

(56) References Cited

FOREIGN PATENT DOCUMENTS

| WO | 2007135505 A2 | 11/2007 |
|----|---------------|---------|
| WO | 2008113149 A2 | 9/2008 |
| WO | 2008152122 A2 | 12/2008 |
| WO | 2009049304 A1 | 4/2009 |
| WO | 2011046853 A1 | 4/2011 |
| WO | 2011107498 A1 | 9/2011 |
| WO | 2011138197 A2 | 11/2011 |

OTHER PUBLICATIONS

"Committee for Veterinary Medicinal Products—Meloxicam (Extension to PIGS)—Summary Report (5)". The European Agency for the Evaluation of Medicinal Products, Veterinary Medicines and Information Technology, Dec. 2000, pp. 1-3.
"Metacam (R) 05 mg/ml oral suspension for cats." Boehringer Ingelheim Datasheet, Web site: http://www.vetgb.com/vetgb_pdfs/metacamc_7a5c_vetgb.pdf> Accessed on Jun. 8, 2010.
"Metacam(R)" FDA Animal & Veterinary Drug Labels, Web site: http://www.fda.gov/downloads/AnimalVeterinary/Products/ApprovedAnimalDrugProducts/DrugLabels/UCM050397.pdf> Accessed Jun. 8, 2010.
"METACAM—Community register of veterinary medicinal products" accessed online at http://pharmacos.eudra.org/F2/register/v004.htm, 2005.
"Types of Solutions". University of Wisconsin, Stevens Point, Feb. 1, 2001, accessed at http://www.uwsp.edu/chemistry/tzamis/chem106pdfs/solutionexamples.pdf, Google date sheet included, 2 pages.
Abstract in English for IT1251650, 1995.
Abstract in English of DE10024752, 2001.
Abstract in English of DE3434707, 1985.
Abstract in English of ES2065846, 1995.
Abstract in English of FR2437838, 1980.
Abstract in English of JP02906528, 1999.
Abstract in English of JP11139971, 1999.
Abstract in English of JP2001170083, 2001.
Abstract in English of JP3550782, 2004.
Abstract in English of JP4018022, 2007.
Abstract in English of JP47007352, 1972.
Abstract in English of WO199301814, 1993.
Altman et al., "Efficacy Assessment of Meloxicam, a Preferential Cyclooxygenase-2 Inhibitor, in Acute Coronary Syndromes Without ST-Segment Elevation: The Nonsteroidal Anti-Inflammatory Drugs in Unstable Angina Treatment-2 (NUT-2) Pilot Study". Circulation, vol. 106, 2002, pp. 191-195.
Ansel et al., "Pharmaceutical Dosage Forms and Drug Delivery Systems". Seventh Edition, Lippincott Williams & Wilkins, Philadelphia, PA, 1999, pp. 77-87.
Bednarek et al., "Effect of steroidal and non-steroidal anti-imflammatory drugs in combination with long-acting oxytetracycline on non-specific immunity of calves suffering from enzootic bronchopneumonia". Veterinary Microbiology, vol. 96, 2003, pp. 53-67.
Bednarek et al., "The effect of steroidal and non-steroidal anti-inflammatory drugs on the cellular immunity of calves with experimentally-induced local lung inflammation". Veterinary Immunology and Immunopathology, vol. 71, 1999, pp. 1-15.
Boehringer Ingelheim; Metacam (Meloxicam) Now Approved for Pigs and Mastitis in Dairy Cows; May 2003 Press Release; pp. 1-2.
Bunji, Kouho, "Tissue Damage Due to Infections". Drug Injection Handbook, Fundamentals of Blending Variation for Injection Drugs, Nanzando Co. Ltd., Tokyo, 1976, p. 5.
Cho et al., "In vitro effects of *Actinobacillus pleuropneumoniae* on inducible nitric oxide synthase and cyclooxygenase-2 in porcine alveolar macrophages". American Journal of Veterinary Research, vol. 64, No. 12, Dec. 2003, pp. 1514-1518.
Clarke et al., "Feline osteoarthritis: a prospective study of 28 cases". Journal of Small Animal Practice, vol. 47, 2006, pp. 439-445.
D'Yakov et al., "Long term use of Tamsulosin (omnic®) in Patients with Chronic Prostatitis". Urologiia, vol. 5, 2002, pp. 10-12.
Del Tacca et al., "Efficacy and Tolerability of Meloxicam, a COX-2 Preferential Nonsteroidal Anti-Inflammatory Drug". Clinical Drug Investigation, vol. 22, No. 12, 2002, pp. 799-818.
Dellabella et al., "Conservative Managment of Juxtavesical Calculi with Tamsulosin". European Urology Supplements, vol. 2, No. 1, 2003, p. 81.
DOW Chemicals Brochure, entitled "Using METHOCEL cellulose ethers for controlled release of drugs in hyrophilic matrix systems." Publication Jul. 2000, Form No. 198-02075-700 AMS, pp. 1-36.
Dunn et al., "Tamsulosin: A Review of its Pharmacology and Therapeutic Efficacy in the Management of Lower Urinary Tract Symptoms". Drugs & Aging, vol. 19, No. 2, 2002, pp. 132-161.
Engelhardt et al., "Meloxicam: Influence on Arachidonic Acid Metabolism". Biochemical Pharmacology, vol. 51, 1996, pp. 21-28.
Ettmayer et al., "Lessons Learned from Marketed and Investigational Prodrugs". Journal of Medicinal Chemistry, vol. 47, No. 10, May 2004, pp. 2393-2404.
European Search Report for EP10155400 dated Jun. 9, 2010.
European Search Report for EP10162015 dated Aug. 30, 2010.
Farkouh et al., "Comparison of lumiracoxib with naproxen and ibuprofen in the Therapeutic Arthritis Research and Gastrointestinal Event Trial (TARGET), cardiovascular outcomes: randomised controlled trial". Lancet, vol. 364, Aug. 2004, pp. 675-684.
Fitzgerald et al., "COX-2 inhibitors and the cardiovascular system". Clinical and Experimental Rheumatology, vol. 19, No. 6, Supp. 25, Nov. 2001, pp. S31-S36.
Fitzpatrick et al., "Recognising and Controlling Pain and Inflammation in Mastitis". Proceedings of the British Mastitis Conference, Axient/Institute for Animal Health, Milk Development Council/Novartis Animal Health, 1998, pp. 36-44.
Gerritsen et al., "Prostaglandin Synthesis and Release from Cultured Human Trabecular-meshwork Cells and Scleral Fibroblasts". Experimental Eye Research, vol. 43, No. 6, 1986, pp. 1089-1102.
Giuliani et al., "Role of Antithrombotic Therapy in Cardiac Disease". Mayo Clinic Practice of Cardiology, Third Edition, Mosby, St. Louis, MO, 1996, pp. 1116-1121.
Gollackner et al., "Increased apoptosis of hepatocytes in vascular occulusion after orthotopic liver transplantation". Transplant International, vol. 13, No. 1, 2000, pp. 49-53.
Gruet et al., "Bovine mastitis and intramammary drug delivery: review and perspectives". Advanced Drug Delivery Reviews, vol. 50, 2001, pp. 245-259.
Gunew et al., "Long-term safety, efficacy and palatability of oral meloxicam at 0.01-0.03 mg/kg for treatment of osteoarthritic pain in cats". Journal of Feline Medicine and Surgery, vol. 10, 2008, pp. 235-241.
Guth et al., "Pharmacokinetics and pharmacodynamics of terbogrel, a combined thromboxane A2 receptor and synthase inhibitor, in healthy subjects". British Journal of Clinical Pharmacology, vol. 58, No. 1, Jul. 2004, pp. 40-51.
Hawkey et al., "Gastrointestinal Tolerability of Meloxicam Compared to Diclofenac in Osteoarthritis Patients". British Journal of Rheumatology, vol. 37, No. 9, 1998, pp. 937-945.
Herbort et al., "Anti-inflammatory Effect of Topical Diclofenac After Argon Laser Trabeculoplasty: Preliminary Results of a Placebo Controlled Study". Klin. Monatsbl. Augenheik, vol. 200, No. 5, May 1992, pp. 358-361.
Hirsch et al, "Investigation on the efficacy of meloxicam in sows with mastitis-metritis-agalactia syndrome". Journal of Veterinary Pharmacology and Therapeutics, vol. 26, 2003, pp. 355-360.
Hydrated Silica Webpage; http://science.kosmix.com/topic/hydrated_silica; Kosmix Corporation, Apr. 21, 2011, pp. 1-14.
International Search Report for PCT/EP2002/013983 mailed Apr. 23, 2003.
Jain et al., "Antiplatelet therapy in acute coronary syndromes without persistent ST-segment elevation". Cardiovascular Drugs and Therapy, vol. 15, No. 5, Sep. 2001, pp. 423-436. [Abstract Only].
Kimura et al., "Effect of cilostazol on platelet agrregation and experimental thrombosis". Arzneimittel-Forschung, vol. 35, No. 7A, 1985, pp. 1144-1149. [Abstract Only].

(56) References Cited

OTHER PUBLICATIONS

Kumar et al., "Comparative Studies on Effect of Some Hydrophilic Polymers on the Dissolution Rate of a Poorly Water Soluble Drug, Meloxicam". Indian Drugs, vol. 39, No. 6, Apr. 2002, pp. 323-329.
Li et al., "Degradation mechanism and kinetic studies of a novel anticancer agent, AG2034". International Journal of Pharmaceutics, vol. 167, 1998, pp. 49-56.
Lieberman et al., "Tablet Formulation and Design" in Pharmaceutical Dosage Forms: Tablets, vol. 1, Second Edition, Marcel Dekker, Inc., New York, New York, 1989, pp. 105-108.
Luger et al., "Structure and physicochemical properties of meloxicam, a new NSAID". European Journal of Pharmaceutical Sciences, vol. 5, 1996, pp. 175-187.
Macdonald Campus of McGill University, "Mastitis in Dairy Cows", published online, Jul. 2003, pp. 1-12.
Masferrer et al., "Cyclooxygenase-2 Inhibitors: A New Approach to the Therapy of Ocular Inflammation". Survey of Ophthalmology, vol. 41, Supp. 2, Feb. 1997, pp. S35-S40.
McDonald et al., "Calpain inhibitor I reduces the activation of nuclear factor-KappaB and Organ Injury/Dysfunction in Hemorrhagic Shock". The FASEB Journal, vol. 15, Jan. 2001, pp. 171-186.
Noble et al., "Meloxicam". Drugs, vol. 51, No. 3, Mar. 1996, pp. 424-430.
Parikh et al., Binders and Solvents, Chapter 4, Handbook of Pharmaceutical Granulation Technology, First Edition, Marcel Dekker,1997, pp. 59-67.
Pharma Projects, Dialog File 928, Accession Nr. 0021312, Diclofenac, InSite Vision, 1996, 5 pages.
Pharmaceutical Excipient Encyclopedia, Yakuji Nippo Ltd., Tokyo, 1994, pp. 2-5.
Physicians' Desk Reference, 55th Edition, Medical Economics Company, Inc., 2001, pp. 981-984 and pp. 1404-1406.
Rantanen et al., "Process Analysis of Fluidized Bed Granulation". AAPS PharmsciTech, vol. 2, No. 4, Article 21, 2001, 8 pages.
Remington: The Science and Practice of Pharmacy, 19th Edition, vol. II, Mack Publishing Company, Easton, Pennsylvania, 1995, p. 1646.
Robson et al., "Intrinsic acute renal failure (ARF) associated with non-steroidal anti-inflammatory drug (NSAId) use in juvenile cats undergoing routine desexing-16 cases 1998-2005". May 2006, Journal of Veterinary Internal Medicine, vol. 20, No. 3, Abst. 109, p. 740.
Rudnic et al., "Oral Solid Dosage Forms"., Gennaro, Editior, Remington's Pharmaceutical Sciences, 18th Edition, Mack Publishing Company, Easton, PA, 1990, pp. 1633-1645 and pp. 1654-1655.
Saha et al., "Effect of solubilizing excipients on permeation of poorly water-soluble compounds across Caco-2 cell monolayers". European Journal of Pharmaceutics and Biopharmaceutics, vol. 50, No. 3, 2000, pp. 403-411, Abstract accessed at http://cat.inist.fr/?aModele=afficheN&cpsidt=798854, accessed on Aug. 13, 2010, 3 pages.
Schneeweis et al., "In Vivo and In Vitro Diclofenac Sodium Evaluation After Rectal Application of Soft Gelatine Capsules Enabling Application Induced Transformation (AIT) into a Seminsolid System of Liquid Crystals (SSLC) for Controlled Release". Pharmaceutical Research, vol. 14, No. 12, Dec. 1997, pp. 1726-1729.
Sciencelab.com, "Lactose, Monohydrate, Spray-Dried Powder, NF". Accessed at http://www.epoxy-paint.net/page/.S/PVAR/10419/SLL1453, Feb. 29, 2008, 2 pages.
Snyder et al., "Corticosteroid Treatment and Trabecular Meshwork Proteases in Cell and Organ Culture Supernatants". Experimental Eye Research, vol. 57, No. 4, 1993, pp. 461-468.
Sorbera et al., "Lumiracoxib Antiarthritic, COX-2 Inhibitor". Drugs of the Future, vol. 27, No. 8, Aug. 2002, pp. 740-747.
Stei et al., "Local Tissue Tolerability of Meloxicam, a New NSAID: Indications for Parental, Dermal and Mucosal Administration". British Journal of Rheumatology, vol. 35, Supp. 1, 1996, pp. 44-50.
Straus et al., "New Evidence for Stroke Prevention: Clinical Applications". The Journal of the American Medical Association, vol. 288, No. 11, Sep. 2002, pp. 1396-1398.
Straus et al., "New Evidence for Stroke Prevention: Scientific Review". The Journal of the American Medical Association, vol. 288, No. 11, Sep. 2002, pp. 1388-1395.
Sunose et al., "The Effect of Cyclooxygenase 2 Inhibitor, FK3311, on Ischemia-Reperfusion Injury in Canine Lung Transplantation". Journal of Heart and Lung Transplantation, vol. 19, No. 1, Jan. 2000, p. 40.
Turck al., "Clinical Pharmacokinetics of Meloxicam". Arzneimittel-Forschung, vol. 47, No. 3, 1997, pp. 253-258.
Tunuguntla et al., "Management of Prostatitis". Prostate Cancer and Prostatic Diseases, vol. 5, No. 3, 2002, pp. 172-179.
Vippagunta et al., "Crystalline solids". Advanced Drug Delivery Reviews, vol. 48, 2001, pp. 3-26.
Wagenlehner et al., "Therapy of Prostatitis Syndrome". Der Urologe [A], vol. 40, No. 1, 2001, pp. 24-28. [English Abstract at p. 25].
Nell et al., "Comparison of vedaprofen and meloxicam in dogs with muskuloskeletal pain and inflammation". Journal of Small Animal Practice, vol. 43, No. 5, May 2002, pp. 208-212 [Accessed at http://www.ncbi.nlm.nih.gov/pubmed/12038853 on Sep. 27, 2013]. Abstract Only, 1 page.
Chemical Abstracts, vol. 118, No. 18, Abstract No. 175803, Columbus, OHion, US May 1993 & JP-A-04 321 624 (Hisamitsu Pharm. Co.Inc., JP), Nov. 11, 1992, 1 page.

* cited by examiner

HIGHLY CONCENTRATED STABLE MELOXICAM SOLUTIONS FOR NEEDLELESS INJECTION

The present invention relates to highly concentrated stable meloxicam solutions for intracutaneous or subcutaneous needleless injection for treating respiratory diseases and inflammation in mammals.

BACKGROUND OF THE INVENTION

Meloxicam (4-hydroxy-2-methyl-N-(5-methyl-2-thiazolyl)-2H-1,2-benzothiazine-3-carboxamide-1,1-dioxide) is an active substance which belongs to the group of NSAIDs (non-steroidal-anti-inflammatory drugs). Meloxicam and the sodium and meglumine salt thereof (N-methyl-D-glucamine salt) are described in EP-A-0 002 482. EP-A-0 002 482 shows, inter alia, the example of a 0.2% injectable solution of meloxicam consisting of the meglumine salt of the active substance, sodium chloride and water.

EP-A-0 945 134 discloses the pH-dependent solubility characteristics of meloxicam and its salts, i.e. the sodium salt, the ammonium salt and the meglumine salt, in aqueous solution. According to this, meloxicam is an active substance which does not dissolve readily in water. The meloxicam salts, particularly the meglumine salt, exhibit improved solubility as the pH increases between 4 and 10, as shown in Table 1 of EP-0 945 134. However, up till now it has only been possible to produce stable, clear, aqueous solutions with a low concentration of meloxicam. In addition to the in situ formation of a meloxicam salt, e.g. meglumine salt, and the addition of solubilisers, these solutions were required to have a pH in the range of maximum possible solubility as well as being reasonably well tolerated and contain a high proportion of organic solvent. Attempts to produce formulations with the same or a similar recipe led to cloudiness of the solution, e.g. if the meloxicam concentrations were higher, e.g. 2%.

WO9959634 A1 describes an eye drop solution containing 0.5% meloxicam but makes no reference to possible meloxicam concentrations over 1%. A commercially available 0.5% meloxicam solution is used in small animals such as dogs, heifers and calves to treat respiratory diseases and inflammation, for example.

An active substance for needleless injection makes it possible for the animal keeper himself to administer a sterile solution to the animal. The requirements imposed on an active substance solution for needleless injection include inter alia small injectable volumes, the possibility of weight-related dosage and maximum possible flexibility in the number of actuation processes per treatment unit. Accordingly, injection volumes of 50 µl per actuation, for example, are technically feasible. For this purpose, as described in DE10010123 A1, a sterile solution may be transferred under aseptic conditions into a sterile cartridge which is then inserted in the metering system.

It has not hitherto been possible to treat large farm animals with a meloxicam solution that could be injected without a needle. The low concentration of active substance in the injectable solution did not allow an acceptable, well tolerated injection volume. The administration of meloxicam solutions by needlefree injection requires that the solution be free from particles, as solutions of this kind are subject to the same requirements as solutions for parenteral administration. In addition to intracutaneous and subcutaneous administration transcutaneous administration should also be taken into consideration, involving administering the substance directly into the blood vessels. This latter route is directly comparable with intravenous administration by injection through a syringe. The method of administration by needle-free injection has a relevant effect on bioavailability, which will be greater than with intracutaneous or subcutaneous administration, as transcutaneous absorption also takes place with needle-free injection. Organic solvents, solubilisers and water-soluble substances can only be used in certain concentrations for reasons of drug tolerance. The problem of the present invention is to produce particle-free highly concentrated meloxicam solutions which are stable over long periods, which are suitable for needleless injection.

DESCRIPTION OF THE INVENTION

Surprisingly, it has been found that highly concentrated meloxicam solutions with a content of active substance ranging from 35 to 100 mg/ml which contain, in addition to a meloxicam salt and certain excipients, another excipient selected from among citric acid, lecithin, gluconic acid, tartaric acid, phosphoric acid and EDTA or the salts thereof, may be produced so as to be particle-free and stable over long periods. The stability was achieved with an unexpectedly small amount of organic solubilisers. The formulation was found to be stable even when subjected to the process of final sterilisation.

This results in the solution to the problem according to the invention, as a formulation of a meloxicam solution which contains, in addition to a meloxicam salt, small concentrations of solubiliser, a preservative, a buffer substance for achieving the optimum pH range and another excipient.

The invention relates, as described in claim 1, to aqueous cyclodextrin-free solutions of meloxicam for needle-free intracutaneous or subcutaneous administration which contain a pharmacologically acceptable meloxicam salt of an organic or inorganic base in a highly concentrated solution with 35 to 100 mg/ml of meloxicam together with suitable excipients. Subclaims 2-14 describe advantageous further features of the invention.

The formulation according to the invention overcomes the problem arising from the prior art of providing a solution of the active substance meloxicam which is suitable for needleless injection, by permitting a high concentration of active substance in a particle-free solution which is stable over the long term, having the composition described hereinafter.

The formulation according to the invention may contain, as the meloxicam salt, the meglumine, sodium, potassium or ammonium salt, preferably the meloxicam meglumine salt.

The solubilisers used may be, for example polyethyleneglycols, polyoxyethylene-polyoxypropylene copolymers (e.g. poloxamer 188), glycofurol, arginine, lysine, castor oil, propyleneglycol, solketal, polysorbate, glycerol, sorbitol, mannitol, xylitol, polyvinylpyrrolidone, lecithin, cholesterol, 12-hydroxystearic acid-PEG660-ester, propyleneglycol monostearate, polyoxy-40-hydrogenated castor oil, polyoxyl-10-oleyl-ether, polyoxyl-20-cetostearylether and polyoxyl-40-stearate or a mixture of sorbitol, mannitol and xylitol, preferably polyethyleneglycols, polyoxyethylene-polyoxypropylene copolymers, glycofurol, polyvinylpyrrolidone, lecithin, cholesterol, 12-hydroxystearic acid-PEG660-esters, propyleneglycol monostearate, polyoxy-40-hydrogenated castor oil, polyoxyl-10-oleyl-ether, polyoxyl-20-cetostearylether and polyoxyl-40-stearate. Particularly preferred are polyethyleneglycols, glycofurol and polyoxyethylene-polyoxypropylene-copolymers, but especially polyethyleneglycols (e.g. Macrogol 300) and polyoxyethylene-polyoxypropylene copolymers (e.g. Poloxamer 188). The preservatives used may be, for example, ethanol, benzoic acid and the sodium or potassium salts thereof, sorbic acid and the sodium or potassium salts thereof, chlorobutanol, benzyl alcohol, phenylethanol, methyl, ethyl, propyl or butyl-p-hydroxybenzoates, phenol, m-cresol, p-chloro-m-cresol or benzalkonium chloride. Particularly preferred are ethanol, benzoic acid and the sodium or potassium salts thereof, sorbic acid and the sodium or potassium salts thereof, chlorobutanol, benzylalcohol, phenylethanol and methyl, ethyl, propyl or butyl p-hydroxybenzoates, but preferably ethanol, benzoic acid and the sodium or potassium salts thereof, sorbic acid and the sodium or potassium salts thereof, but especially ethanol.

The buffer system used to achieve a pH of between 8 and 10 may be, for example, glycine, a mixture of glycine and HCl, a mixture of glycine and sodium hydroxide solution, and the sodium and potassium salts thereof, a mixture of potassium hydrogen phthalate and hydrochloric acid, a mixture of potassium hydrogen phthalate and sodium hydroxide solution or a mixture of glutamic acid and glutamate. Glycine, a mixture of glycine and HCl and a mixture of glycine/sodium hydroxide solution, especially glycine, are particularly preferred.

Other suitable excipients are citric acid, lecithin, gluconic acid, tartaric acid, phosphoric acid and EDTA or the alkali metal salts thereof, preferably tartaric acid and EDTA or the alkali metal salts thereof, particularly disodium EDTA.

One embodiment of the invention contains, in addition to the meglumine or sodium salt of the meloxicam, polyethyleneglycols, glycofurol and/or polyoxyethylene-polyoxypropylene copolymers, but particularly polyethyleneglycols (e.g. Macrogol 300) and/or polyoxyethylene-polyoxypropylene copolymers (e.g. Poloxamer 188) as solubiliser, ethanol, benzoic acid and the sodium or potassium salts thereof or sorbic acid and the sodium or potassium salts thereof, but particularly ethanol, as preservative, and glycine, a mixture of glycine/HCl or a mixture of glycine/sodium hydroxide solution, but preferably glycine, as buffer and disodium EDTA as an additional excipient.

The formulation according to the invention may contain meloxicam in a concentration of 35-100 mg/ml, preferably 40-80 mg/ml, preferably 45-70 mg/ml, particularly preferably 50-60 mg/ml, especially 55 mg/ml.

The meglumine concentration may be between 30 and 50 mg/ml, preferably 35-45 mg/ml, preferably 38-42 mg/ml, especially about 40 mg/ml. The possible sodium, potassium and ammonium concentrations are calculated accordingly.

The concentration of the solubilisers may be in the range from 20-200 mg/ml, preferably 30-150 mg/ml, preferably 40-130 mg/ml, more preferably 50-120 mg/ml, especially 70-100 mg/ml.

The concentration of the preservative ethanol may be in the range from 100-200 mg/ml, preferably 120-180 mg/ml, more preferably about 150 mg/ml.

The concentration of the preservatives benzoic acid and the sodium or potassium salts thereof, sorbic acid and the sodium or potassium salts thereof, chlorobutanol, benzyl alcohol, phenylethanol, phenol, m-cresol and p-chloro-m-cresol may be in the range from 0.5-50 mg/ml, preferably 1-10 mg/ml, more preferably 3-5 mg/ml.

The concentration of the preservatives benzalkonium chloride, phenylmercury nitrate and methyl-, ethyl-, propyl- or butyl-p-hydroxybenzoates may be in the range from 0.01-4 mg/ml, preferably 0.02-3 mg/ml, more preferably 0.1-0.5 mg/ml.

The concentration of the buffer substances may be between 4 and 138 mg/ml, preferably between 5 and 20 mg/ml, more preferably between 8 and 10 mg/ml.

The concentration of the other excipients mentioned above, i.e. EDTA, citric acid, lecithin, gluconic acid, tartaric acid and phosphoric acid or the salts thereof may be in the range from 0.2-3 mg/ml, preferably 0.3-2.5 mg/ml, preferably 0.5-2 mg/ml, most preferably 0.6-1.5 mg/ml, and in particular 0.7-1.0 mg/ml.

Meglumine and meloxicam may be used in a molar ratio of between 9:8 and 12:8, preferably in a molar ratio of 11:8, but especially in a molar ratio of 10:8.

In the formulation according to the invention, meloxicam and the other excipient, particularly disodium EDTA, may be present in a weight ratio of between 100:1 and 35:1, preferably between 80:1 and 40:1, preferably between 70:1 and 45:1, more preferably between 60:1 and 50:1, most preferably between 58:1 and 52:1, in particular about 55:1.

The formulation according to the invention may have a shelf-life after opening of 28 days or more.

The shelf-life of the solution in the sealed original packaging may be 1 month or more, in particular between 1 month and 24 months, but at least between 1 month and 18 months, preferably between 1 month and 12 months, more preferably between 1 month and 9 months, most preferably between 1 month and 6 months, particularly between 1 month and 3 months.

The formulation according to the invention should have a pH of between 8 and 10, preferably between 8.5 and 9, more preferably a pH between 8.7 and 8.9, particularly 8.8.

The formulation according to the invention is suitable for treating pain, inflammation, fever, acute mastitis, diarrhoea, lameness, oncological indications, problems with the locomotor apparatus, and respiratory complaints in animals, preferably acute mastitis, diarrhoea, lameness, problems with the locomotor apparatus and respiratory complaints, especially acute mastitis, diarrhoea, lameness, problems with the locomotor apparatus and respiratory complaints, most preferably respiratory complaints and oncological indications. The treatment may be given in conjunction with antibiotic therapy.

The formulation according to the invention is suitable for treating animals, preferably mammals, more particularly domestic pets, working animals or farm animals.

The formulation according to the invention is suitable for treating animals, preferably animals up to 500 kg, particularly domestic pets from 1 kg upwards, more preferably from 2 to 70 kg, most preferably 5 to 60 kg, or large animals up to 750 kg, preferably 50 kg to 500 kg, most preferably 100 to 400 kg.

The dosage of the formulation according to the invention should correspond to 0.1 to 1.0 mg of active substance per kg of bodyweight, preferably 0.4 to 0.8 mg/kg of bodyweight, more preferably 0.5 to 0.7 mg/kg of bodyweight, particularly preferably 0.6 mg/kg of bodyweight.

The formulation according to the invention may be prepared using the methods of preparing aqueous liquid formulations known from the literature. For example, the appropriate excipients may be added to a meloxicam salt solution.

Various commercial materials for aqueous liquid formulations which will allow sealing under inert gas and/or final sterilisation by autoclaving in the finished container may be used as a packaging material for the formulation according to the invention. Such materials include for example ampoules or glass vials, particularly glass vials, e.g. 50 ml or 100 ml glass vials of glass Type I (according to Pharm. Eur/USP) in conjunction with rubber stoppers made of ethylenepropylenenorbornene terpolymer (EPDM) and aluminium caps. Vials made of plastics, particularly COC (Cyclic Olefin Copolymer), and other types of rubber stoppers are also suitable.

The meloxicam solutions according to the invention will now be illustrated by the following Example. Anyone skilled in the art will be aware that the Example serves only as an illustration and is not to be regarded as restrictive.

EXAMPLE

4% meloxicam solution

| Ingredients: | g/100 ml |
| --- | --- |
| Meloxicam | 4.0 |
| Meglumine | 2.8 |
| Macrogol 300[*1] | 15.0 |
| Poloxamer 188[*2] | 5.0 |
| Ethanol | 15.6 |
| Glycine | 0.5 |
| EDTA-Na | 0.1 |
| 1M HCl | q.s. ad pH 8.8 |
| 1M NaOH | q.s. ad pH 8.8 |
| Water for injections | ad 100 ml |

[*1]obtainable from Brenntag, Plochingen, Germany
[*2]obtainable from C. H. Erbsloeh, Krefeld, Germany For example, dogs may be treated by needle-free injection with a 4% meloxicam solution according to the invention in a metered volume of 50 μl per spray jet in a precise dosage related to body weight. A dog weighing 10 kg can be treated with a dose of 0.2 mg of meloxicam per kg of body weight with precisely one spray jet. Therapeutic accuracy is ensured in this case in steps of 10 kg.

Method of Preparation 4 g of meloxicam are dissolved in 50 ml of an aqueous meglumine solution (1.4 g/50 ml) at 90° C. The other excipients are added one after another to the solution according to the recipe given above. The pH is then adjusted to 8.8 using 1M hydrochloric acid and 1M sodium hydroxide solution. Water is added to the solution until a volume of 100 ml is obtained.

The invention claimed is:

1. An aqueous particle free highly concentrated meloxicam solution suitable for administration by needleless injection, comprising:
   40 to 80 mg/ml meloxicam;
   meglumine in amount such that the meglumine and meloxicam are present in a molar ratio of between 9:8 and 12:8;
   disodium EDTA in an amount such that the weight ratio of meloxicam to disodium EDTA is between 100:1 and 35:1;
   a polyethylene glycol;
   a polyoxyethylene-polypropylene copolymer; and
   ethanol;
   wherein the solution is free of cyclodextrin, the solution has a pH of between 8.5 and 9, and the solution has a shelf-life after opening of 28 days or more.

2. The aqueous solution according to claim 1, wherein the meglumine and meloxicam are present in a molar ratio of 10:8.

3. The aqueous solution according to claim 1, further comprising glycine.

4. The aqueous solution according to claim 1, wherein the solution comprises meloxicam, meglumine, a polyethyleneglycol, a polyoxyethylene-polyoxypropylene copolymer, ethanol, glycine, disodium EDTA, and water suitable for injection.

5. The aqueous solution according to claim 4, wherein the solution further comprises sodium hydroxide or hydrochloric acid.

6. The aqueous solution according to claim 1, further comprising a buffer or a preservative.

7. The aqueous solution according to claim 1, further comprising a solubilizer.

8. The aqueous solution according to claim 1, wherein the solution has a long term shelf-life of 24 months or more in its original packaging.

9. A sterile cartridge containing a solution according to claim 1.

* * * * *